United States Patent
Trillon et al.

(10) Patent No.: US 10,215,011 B2
(45) Date of Patent: Feb. 26, 2019

(54) PIPELINE ELEMENT FITTED WITH A MONITORING SYSTEM

(71) Applicant: VALLOUREC TUBES FRANCE, Boulogne Billancourt (FR)

(72) Inventors: Adrien Trillon, Le Quesnoy (FR); Emmanuel Desdoit, Maubeuge (FR); Sebastien Petit, Thumeries (FR)

(73) Assignee: VALLOUREC TUBES FRANCE, Boulogne Billancourt (FR)

( * ) Notice: Subject to any disclaimer, the term of this patent is extended or adjusted under 35 U.S.C. 154(b) by 310 days.

(21) Appl. No.: 14/653,126

(22) PCT Filed: Dec. 17, 2013

(86) PCT No.: PCT/FR2013/053110
§ 371 (c)(1),
(2) Date: Jun. 17, 2015

(87) PCT Pub. No.: WO2014/096667
PCT Pub. Date: Jun. 26, 2014

(65) Prior Publication Data
US 2015/0330206 A1    Nov. 19, 2015

(30) Foreign Application Priority Data

Dec. 18, 2012  (FR) .................... 12 62237

(51) Int. Cl.
*G01N 29/24* (2006.01)
*E21B 47/00* (2012.01)
(Continued)

(52) U.S. Cl.
CPC ........ *E21B 47/0006* (2013.01); *F16L 11/127* (2013.01); *F16L 55/07* (2013.01);
(Continued)

(58) Field of Classification Search
CPC ..... E21B 47/0006; F16L 11/127; F16L 55/07; G01N 17/04; G01N 29/04; G01N 29/11;
(Continued)

(56) References Cited

U.S. PATENT DOCUMENTS 5,035,143 A * 7/1991 Latimer ............... G01N 29/041
367/127
2001/0022514 A1 9/2001 Light et al.
(Continued)

FOREIGN PATENT DOCUMENTS

EP  1 467 060  10/2004
GB  2 403 009  12/2004
(Continued)

OTHER PUBLICATIONS

International Search Report dated Feb. 11, 2014 in PCT/FR2013/053110 filed Dec. 17, 2013.

*Primary Examiner* — Manish S Shah
*Assistant Examiner* — Rose M Miller
(74) *Attorney, Agent, or Firm* — Oblon, McClelland, Maier & Neustadt, L.L.P.

(57) ABSTRACT

An element configured to be mounted at an end of a pipe suited to circulation of a fluid to extend the pipe. The element includes a hollow profiled body including a peripheral surface and a protective covering at least partially covering the peripheral surface. The element further includes a sensor of guided waves type, control electronics for the guided wave sensor, and an electric cable configured to connect the control electronics to corresponding electronics of the pipe. The electric cable and the guided wave sensor are fixed to the peripheral surface of the body under at least part of the protective covering.

12 Claims, 4 Drawing Sheets

(51) Int. Cl.
  *G01N 17/04*   (2006.01)
  *G01N 29/04*   (2006.01)
  *F16L 55/07*   (2006.01)
  *G01N 29/22*   (2006.01)
  *F16L 11/127*  (2006.01)
  *G01N 29/11*   (2006.01)

(52) U.S. Cl.
  CPC .............. *G01N 17/04* (2013.01); *G01N 29/04* (2013.01); *G01N 29/11* (2013.01); *G01N 29/223* (2013.01); *G01N 29/2412* (2013.01); *G01N 2291/0234* (2013.01); *G01N 2291/0289* (2013.01); *Y10T 29/49828* (2015.01)

(58) Field of Classification Search
  CPC ... G01N 2291/0234; G01N 2291/0289; G01N 29/223; G01N 29/2412
  USPC ........................................ 73/643, 642, 622
  See application file for complete search history.

(56) References Cited

U.S. PATENT DOCUMENTS

| | | |
|---|---|---|
| 2002/0035437 A1 | 3/2002 | Tingley |
| 2002/0078759 A1 | 6/2002 | Bray |
| 2002/0134161 A1 | 9/2002 | Chinn |
| 2004/0200613 A1 | 10/2004 | Fripp et al. |
| 2004/0255678 A1 | 12/2004 | Nagashima et al. |
| 2007/0206440 A1 | 9/2007 | Fripp et al. |
| 2010/0052669 A1* | 3/2010 | Kwun .................. G01N 29/043 324/240 |
| 2010/0052670 A1* | 3/2010 | Kwun ................ G01N 29/2412 324/240 |
| 2012/0291554 A1* | 11/2012 | Baba .................... G01N 29/228 73/632 |
| 2013/0036822 A1* | 2/2013 | Daikoku ............ G01N 29/2412 73/632 |
| 2013/0125655 A1 | 5/2013 | Klopffer et al. |
| 2013/0179098 A1 | 7/2013 | Vogt |
| 2014/0144238 A1* | 5/2014 | Luo ...................... G01N 29/223 73/590 |

FOREIGN PATENT DOCUMENTS

| | | |
|---|---|---|
| GB | 2 482 300 | 2/2012 |
| GB | 2 489 107 | 9/2012 |
| WO | 02 10709 | 2/2002 |
| WO | 2012 004508 | 1/2012 |

* cited by examiner

PIPELINE ELEMENT FITTED WITH A MONITORING SYSTEM

The invention relates to the long-term monitoring of pipelines intended for the circulation of fluids, of the type produced by connecting together elementary pipes and/or other hollow profiles.

Pipelines of this type include, for example, those known as "risers", which link an oil platform with the seabed, "pipelines", which serve in particular to carry petroleum and natural gas, or also the pipelines used to transport water at very high temperature into power stations.

The elementary pipes and the pipelines formed from these pipes have a covering on the outside, principally to protect them from their environment.

The monitoring of these pipelines generally involves detecting, locating and/or assessing defects in the pipeline's walls such as, for example, fatigue cracks which appear in the form of fine cracks extending transverse to the pipeline, pitting corrosion which takes the form of spherical depressions, and all types of abnormalities which have analogous geometric characteristics. Such defects generally occur on the internal surface of the pipeline, but external defects also exist. The welded joints which ensure that the elementary pipes are bonded together are sites of particular interest for the monitoring of a pipeline, because the defects are more likely to form there and are potentially more dangerous there than in the rest of the pipeline.

In the long term, i.e. over a period close to the life of the pipeline, the appearance of new defects and/or the evolution of already known defects are monitored, on the elements of the pipeline themselves and on the bonding welded joints. Typically this involves regularly performing checks on the whole of the pipeline and comparing the results of these checks with each other.

For the purposes of simplifying the disclosure, reference is made here to the field of subsea pipelines, used in the offshore sector. It is understood that this in no way limits the scope of the invention, which can be used in the onshore sector, in particular in the case of constraints similar to those which characterize the offshore sector, for example difficulties with access to the pipeline, stability over time of said pipeline, the nature of the defects monitored and/or the aggressive nature of the surrounding medium. There may be mentioned for example the case of buried pipelines, situated in areas with a high level of radioactivity or unstable areas, in particular areas having a high seismic risk.

The pipelines installed in the offshore sector link the seabed, on which they can optionally partially rest, with a platform on the surface.

It is known to use, as sensors, optical fibres which run along the pipeline, up to the platform. Sensors of the optical fibre type make it possible for example to assess mechanical stresses to which the pipeline is subjected, in particular bending stresses, or also temperatures. Although the optical fibres and optical fibre sensors prove to be effective for monitoring the mechanical strength of the pipeline as a whole or also for measuring the temperature of the pipeline, it is not known to use them to detect defects of the above-mentioned type.

For these latter, sensors are used which are arranged to transmit what are known as "guided" sound waves, which propagate along the pipeline and the behaviour of which will be disrupted in the presence of geometric irregularities, in particular defects. By studying the echoes resulting from these sound waves it is possible to detect the existence of a defect and, by comparison with previously recorded echoes, to describe its evolution over time.

Waves which propagate in a favoured direction, while their energy remains limited within a confined area in the directions transverse to this direction of propagation, are described as "guided".

In particular mechanical waves, for example torsion waves, which are made to propagate parallel to the longitudinal direction of the products, are used to check elongate metal products, in particular pipes.

Guided waves are usually generated by means of mechanical pulses transmitted from a sensor to the metal product to be checked.

The document "*Permanently Installed Monitoring System Overview*" from Guided Ultrasonic Ltd. discloses an inspection system based on an ultrasonic sensor. This system comprises a transducer permanently installed in one location on the pipeline and which can be excited to monitor all of a length of this pipeline. This system, called "g-PIMS", moreover comprises a bundle, described as umbilical, which comprises a cable directly connecting the ultrasonic transducer to a control room on the offshore platform, or to the surface in the case of a buried pipeline. Generally, the cable is free, and does not necessarily follow the pipeline.

According to the authors of the document in question, the g-PIMS system makes it pointless and very expensive to use "ROV", for "Remotely Operated Vehicle", robots and other submersion operations. This system makes it possible to compare data collected shortly after the submersion of the pipeline with data acquired by the same sensor one or more years later. The authors of the document believe that their system makes it possible to verify the integrity of the pipeline in the long term.

The document "*Technology Insight Inspection of Subsea & Un-piggable Pipelines*" from Subsea Integrity Group, or SIG for short, discloses variants of and/or additions to the g-PIMS system. In particular it relates to submersion equipment for deploying the system, an annular transducer housed in an epoxy mould with an umbilical cable which runs along the surface of the pipeline, or also ROV robots equipped so as to make such inspections possible.

Moreover, the document WO 02/093155 A1, in the name of Southwest Research Institute, discloses a system based on magnetostrictive sensors. These sensors, generally numbering four, are mounted around a pipeline which is buried. Each sensor is connected individually to a junction box situated on the surface.

In the above technologies, each sensor is connected individually, by a cable comprised within the "umbilical" bundle, to control electronics situated on the surface. Because of the difficulties in connecting each sensor to control electronics, installing the sensor or sensors on the pipeline in a manner that allows both their good operation and their stability over time, or also in supplying power to these sensors, the technologies in question provide for either a single sensor or several sensors grouped together in one and the same location on the pipeline. This limits these technologies to operation at low frequencies, typically below 60 kilohertz, the only way to allow long lengths of pipelines, capable of reaching several hundred meters, to be inspected when the background noise is weak. When the level of background noise is high, for example in the presence of accessories on the pipeline or generalized corrosion, only a few tens of meters, or even only a few meters, of pipeline can be inspected.

All things being equal, moreover, the use of low frequencies is detrimental to the detection of defects with small dimensions, and in particular fine defects, i.e. with a width (dimension in the longitudinal direction of the pipeline) smaller than 1 millimeter. The defects often encountered in welds include fatigue cracks, which generally have a very small width. In order to detect fine defects, the Applicant has found that it is necessary to use high frequencies, above 100 kilohertz in particular.

In other words, the higher the frequency, the greater the amplitude of the echo, but more sensitivity is lost with the distance separating the sensor from the defect.

The Applicant set himself the aim of monitoring the majority of the defects that can occur in a pipeline by developing a system which is, all at once, simple to integrate, inexpensive, easy to power, and which can be installed simply on the pipeline.

An element is proposed which is intended to be mounted at one end of a pipeline suitable for the circulation of fluid in order to extend said pipeline, the element comprising a hollow profile body having a peripheral surface, a protective covering at least partially covering said peripheral surface. The proposed element moreover comprises a sensor of the guided wave type, control electronics for the guided wave sensor and at least one electrical cable arranged to connect the control electronics to homologous electronics of said pipeline. The electrical cable and the guided wave sensor are fixed to the peripheral surface of said body, under at least a part of the protective covering.

A pipeline is also proposed which is suitable for the circulation of fluid and comprises elements joined together end to end and each comprising a hollow profile body having a peripheral surface, a protective covering at least partially covering said peripheral surface. At least some of said elements comprise a sensor of the guided wave type fixed to the hollow profile body, and control electronics for this guided wave sensor. The pipeline moreover comprises electrical cables connecting the control electronics to each other. The electrical cables and the guided wave sensors are fixed on the peripheral surface of a respective body, under at least a part of the protective covering.

A method of manufacturing the proposed element is also proposed which comprises fixing at least one electrical cable and one sensor of the guided wave type on a peripheral surface of a hollow profile body, applying at least one layer of protective covering to the guided wave sensor and the electrical cable, and fixing control electronics for the guided wave sensor to the hollow profile body and linking these electronics to one end of at least one of the electrical cables.

A method is moreover proposed for extending a pipeline suitable for the circulation of fluid comprising a terminal element comprising a hollow profile body having a peripheral surface and a protective covering at least partially covering the peripheral surface, a sensor of the guided wave type and control electronics for the guided wave sensor, in which an electrical cable is connected to the control electronics, the electrical cable and the magnetostrictive sensor being fixed on the peripheral surface of said body, under at least a part of the protective covering. The proposed method comprises providing an extension element having a hollow profile body having a peripheral surface and a protective covering at least partially covering the peripheral surface, a sensor of the guided wave type and control electronics for the guided wave sensor. An electrical cable is connected to the control electronics. The electrical cable and the magnetostrictive sensor are fixed on the peripheral surface of said body, under at least a part of the protective covering. The body of the extension element is then welded to the body of the terminal element. Finally, the electrical cable of the terminal element is connected to that of the extension element.

Finally, a method is proposed for forming a segment of pipeline suitable for the circulation of fluid comprising at least two homologous pipeline elements joined together, each of these homologous pipeline elements comprising a hollow profile body having a peripheral surface, a protective covering at least partially covering said peripheral surface, a sensor of the guided wave type and control electronics for the guided wave sensor, in which at least one electrical cable connects the control electronics of one of the homologous pipeline elements to the control electronics of the other of these pipeline elements, the electrical cable and the guided wave sensors being fixed on the peripheral surface of said bodies, under at least a part of the protective covering. The method comprises providing two homologous pipeline elements each having a hollow profile body having a peripheral surface, a protective covering at least partially covering said peripheral surface, at least one electrical cable and one sensor of the guided wave type, the electrical cable and the guided wave sensor being fixed on the peripheral surface of said body, under at least a part of the protective covering; welding the body of one of the homologous elements to the body of the other of these elements; connecting the electrical cable of the homologous pipeline elements together, or the cables of one of the homologous pipeline elements to control electronics of the other of these elements, in a part of this cable that is detached from the body and/or which extends beyond the protective covering.

The proposed pipeline element can be checked regularly and frequently. It allows an effective detection, not only of the defects linked to corrosion or plugs being formed, but also of defects linked to fatigue, in particular of the crack type, at the level of the welded joints, thanks to:
- a guided wave sensor from which a reference signal, for example the signal reflected by a defect-free welded joint, can be derived. This reference signal in practice cannot be obtained by simulation or predicted in any way, because the signal reflected by a welded joint, in particular for offshore transport pipes, is largely influenced by the existence of (internal or external) beads on the welded joint or differences in shape between the pipes welded together;
- a sensor, in each case relatively close to a welded joint, typically at a distance of less than 4 meters, which can be used at high frequencies that are more sensitive to the defects being searched for;
- once the pipeline elements have been connected together, sensors arranged consecutively to each other which make it possible to confirm the presence of a defect by cross-checking data.

The installation of the sensor, prior to connecting the pipeline element, is inexpensive compared with the cost of fixing in situ, in particular offshore. Thus, in practice, there is no longer a limit to the number of sensors that can be installed on the pipeline. Defects which require a short inspection distance (high frequencies, sensitivity relative to attenuation, in particular for covered pipes) can be searched for. The sensors and their control electronics can be automatically calibrated, after installation of the elements in the pipeline.

Guided waves are generated in the pipe, under the covering.

The control electronics can in each case be connected to neighbouring electronics in order to make it possible to relay information and electric power from the electronics in question.

Once the pipeline has been put in place, the use of several adjacent sensors makes it possible to cover the blind area of each sensor. The blind area of a sensor is generally comprised between 30 and 50 centimeters and, in certain cases, can reach 1 meter, on both sides thereof.

The use of adjacent sensors and electronics arranged in a network makes it possible to obtain information about the distance between the sensors. This distance is fixed throughout the life of the pipeline and can therefore be used advantageously in order to calibrate the speed of the guided waves propagating between the sensors. This distance information makes it possible to correct the effects of any variations in temperature and other phenomena likely to alter the speed of the waves in the pipes. A coefficient of expansion/compression can be calculated between a signal taken as reference and a subsequent signal, such that the difference between them makes it possible to show the appearance, or not, of an additional peak revealing the presence of a defect.

It is also possible to correct the receiving gain relative to a given reference state, in order to compensate for the attenuation of the received signal, over time. Such an attenuation can occur, for example, because of the corrosion of the steel, possible loss of effectiveness of the coupling of the sensor, because of the viscosity of the internal product being transported or also an evolution of the covering.

The use of adjacent sensors makes it possible to implement the technique called "pitch catch", according to which one sensor operates in transmission while a different sensor operates in reception, in order to measure an attenuation value, to calibrate the sensors relative to each other, to detect the presence of a defect through the disturbance of a transmitted wave rather than by reflection, or also to measure the residual thickness of the pipeline. It is also possible to confirm that a sensor is operating well by using an adjacent sensor to listen.

The location of a defect is simplified when several adjacent sensors are used. It is no longer necessary to use the technique called "direction control".

It is no longer necessary to implement the technique, known as direction control, which strictly imposes a relationship between the working frequency and the distance between two coils. Thus, the sensor can be constituted by a single coil, which again makes it possible to use the sensor at all of the desired frequencies, without manipulation.

By using several consecutive sensors, it is possible to use several transmission frequencies without manipulating these sensors, while maintaining the ability to locate the defects.

Some conventional systems provide for guided wave sensors arranged on top of the covering of the pipeline. In the offshore sector, linking the sensors of the conventional systems involves the use of subsea means in order to connect each of these systems to one and the same data processing station on the surface. As the conventional systems are arranged on top of the covering, the detection of defects by guided waves is not satisfactory.

It is the case that the conventional systems are arranged directly on the steel which constitutes the pipe. In this case, it is necessary to remove a part of the covering, fix the system on the pipeline, in contact with the steel, and embed the system in question in epoxy resin, which proves to be a delicate and expensive operation. In practice, this method of fixing is reserved for the pipes which are located out of the water. For the others, the systems should be arranged under the covering, which constitutes a delicate and expensive, or even impossible, operation which involves removing the covering, fixing the sensor and reconstructing the covering on top of it.

In the proposed element, the electrical bundle is located under the covering, before the installation operations. The connections between the electronics of adjacent pipes are made during the welding of these pipes, before what is called in the art the "laying", i.e. the placement of the pipe or the pipeline on the seabed or other. The connection produced in this way can be protected in the same manner as the welded joint, by means of a covering produced on top of the welded joint, for example of the type known as "field joint coating". Only the pipe situated at the end of the pipeline, which can be located out of the water, has a connection which connects it to the control and data processing station. In the case where only one section of the pipeline is formed of elements of the proposed type, the control electronics of the element of the section closest to the platform, which can be submerged, can be connected to this platform via an umbilical.

Other features and advantages of the invention will become apparent on examination of the detailed description that follows, and the attached drawings, in which.

The attached drawings are largely of a definite character. As a result they will be able not only to serve to better explain the description detailed hereinafter, but also to contribute to the definition of the invention, as appropriate.

Figure 1:
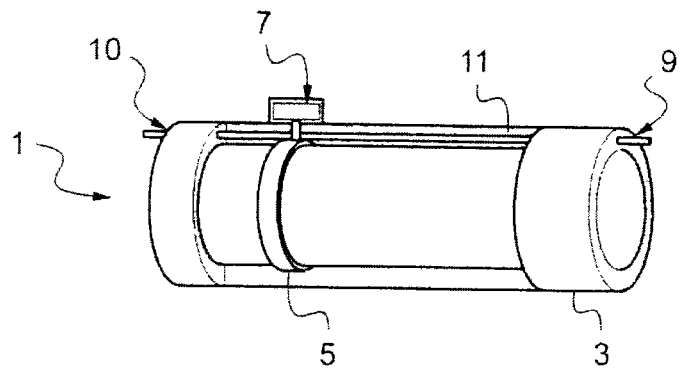
FIG. 1 shows a pipeline element according to the invention, seen in perspective and partially cutaway.

Reference is made to FIG. 1.

A pipeline element 1 comprises a bare elementary pipe 3 equipped with a guided wave sensor 5 which surrounds the elementary pipe 3 transversally. The guided wave sensor 5 is held fixedly in contact with the external surface of the elementary pipe 3 via a fixing medium. Here, the fixing medium comprises a layer of adhesive material applied to a part of the external surface of the elementary pipe 3 which is located facing the guided wave sensor 5.

The fixing medium is such that it can transmit mechanical pulses from the sensor 5 to the pipe 3, in particular capable of generating torsion waves in the wall of the elementary pipe 3. The fixing medium serves as a coupling medium between the sensor 5 and the elementary pipe 3. For example, the sensor 5 is glued to the external surface of the pipe 3, in particular by means of an electrically nonconductive glue, based on epoxy resin, for example the one known as "araldite". Other adhesive materials can be used, in particular of the solid type and with a high modulus of elasticity, typically greater than 5,000 megapascals.

The adhesive materials which can be used comprise the products known under the following names: Pyro-Putty 2400 (ceramic glue) for use at high temperature, MP55310 (two-component methacrylate glue) for a marine application, Loctite 3455 (epoxy glue), double-sided acrylic foam adhesive with a thickness of 0.2, 0.5 or 0.8 millimeters.

As a variant, the sensor 5 can be attached to the pipe by means of a very firmly tightened strap.

The fixing medium allows indirect contact between the sensor 5 and the external surface of the pipe 3.

Preferably, the fixing medium is such that it also acts as an electrical insulator in order to prevent galvanic corrosion phenomena, which are likely to increase the corrosion of the elementary pipe 3. For example, the fixing medium can comprise glass fibres embedded in a layer of epoxy resin.

The sensor 5 is fixed permanently.

The sensor 5 is arranged, relative to the pipe 3, in such a way that the waves that it generates propagate preferentially in the longitudinal direction of the pipe 3. The sensor 5 is in the form of a strip which surrounds the pipe 3 transversally.

Of the sensors capable of producing guided waves, in particular sensors of the piezoelectric type, sensors of the magnetostrictive type or also sensors of the electromagnetic acoustic type are known.

As shown in FIG. 1, the pipeline element 1 is ready to be connected to an analogous pipeline element in order to form a section of pipeline.

The pipeline element 1 is moreover equipped with on-board electronics 7 which are held fixedly on the elementary pipe 3, at the external surface thereof. The on-board electronics 7 ensure the operation of the guided wave sensor 5, in transmission and/or in reception. The on-board electronics 7 are capable of being connected to analogous on-board electronics, equipping elements of a pipeline, so as to allow data to be communicated between these electronics and a power supply.

The pipeline element 1 comprises a first electrical bundle 9 and a second electrical bundle 10. One end of each of the electrical bundles 9 and 10 is connected to the on-board electronics 7, while, in each case, the other end of these bundles terminates close to a respective end of the elementary pipe 3. The electrical bundles 9 and 10 are held fixedly at the surface of the elementary pipe 3, over the majority of their length. Here, the bundles 9 and 10 extend along one and the same generator of the elementary pipe 3. However, the bundles 9 and 10 can be wound around the elementary pipe 3, in a spiral, in order to improve their mechanical resistance. Each of the bundle 9 and the bundle 10 can be doubled with a homologous bundle (not shown in the figures), which acts as an auxiliary bundle.

The pipeline element 1 comprises a protective covering 11 which covers the free external surface of the elementary pipe 3 and of which at least a part covers the sensor 5, the first electrical bundle 9 and the second electrical bundle 10. The first bundle 9 and the second bundle 10 can be embedded in the protective covering 11, which then participates in the fixing of these bundles relative to the elementary pipe 3.

The covering 11 can comprise one or more layers of one or more materials intended to ensure the protection of the pipeline element 1 in its medium of use, in particular vis-à-vis corrosion phenomena. At least one of the layers of the covering 11 covers the sensor 5 and the free external surface of the elementary pipe 3.

The covering preferably comprises a layer of epoxy resin, which serves in particular to fix the sensor 5, and one or more layers of a thermally insulating material which cover the sensor 5. For example the covering can comprise three layers of protection against corrosion and two layers of thermal insulation, in particular in the case of very low external temperatures such as is the case for deep offshore applications (deeper than 2,000 or 3,000 meters). Here, the thickness of the covering 11 is such that it allows cables and/or a part of the sensor 5 to be housed in it. This thickness is for example comprised between 3 and 10 millimeters.

The choice of the thickness of the covering 11 depends on different criteria. Usually it is the imagined application, and more particularly the nature of the medium in which the pipeline element 1 will be placed, that determines the protection to be given to the elementary pipe 3 and therefore the nature and the thickness of the covering 11. The Applicant has found that the fact of placing the guided wave sensor 5 under at least a part of the covering 11 would greatly improve the performance of said sensor. This improvement in performance is particularly critical when the sensor 5 is working in reception, because the received signals are generally of low amplitude.

In every case, the act of covering the guided wave sensor 5 with at least a part of the covering 11 protects the sensor 5.

The covering 11 is for example of the type known as 3LPE coating or the one known as 3LPP coating. In these cases, the first layer of the covering is advantageously used as adhesive for fixing the sensor 5.

The portions of the elementary pipe 3 close to the ends of the latter can be free of covering 11 in order to facilitate the connection of the pipeline element 1 to other pipeline elements, in particular by welding.

The electronics 7 can be housed, at least partially, in the thickness of the covering 11.

The electronics 7 and the sensor 5 are connected together in an operative manner. The electronics 7 ensure the excitation of the sensor 5.

The link between the sensor 5 and the electronics 7 can use at least one of the following elements:
  one or more wires or cables passing through the covering 11;
  one or more contact traces for connecting the sensor to a metallized surface of the covering, itself connected to the electronics 7;
  one or more flat sockets, optionally glued to the covering 11;
  a wireless link, for example by means of an induction loop.

The electronics 7 can be fixed to the elementary pipe 3, for example by means of an intermediate part forming a flat surface. Preferably, the flat surface comprises connection sockets for linking the electronics 7 to the sensor 5. The intermediate part can also take the form of a belt, wound around the pipe 3.

Here, the sensor 5 equipping the pipeline element 1 is arranged close to one of the ends of the elementary pipe 3, which makes it possible to distinguish the echoes respectively produced by the end welded joints and therefore to locate a defect. For example, when the elementary pipe 3 has a length of 12 meters, the Applicant found that it was expedient to arrange the guided wave sensor 5 at approximately 2.2 meters from one of the ends of the elementary pipe 3.

In general, it is advantageous to arrange the sensor as close as possible to the end of the pipeline element 1 in order to better locate the defects which could occur in a welded joint produced at this location. However, the welding operations which are likely to damage the sensor 5 and the existence of an area close to the sensor in which the latter is "blind" means that it is not expedient to arrange the sensor too close to this end. For example the sensor can be arranged at a distance greater than 30 centimeters from one of the ends of the elementary pipe 3.

Locating a close welding echo also makes it possible, with knowledge of the installation distance of the sensor relative to its end, for example 2.2 meters, to estimate the length of the pipes and the distance between each sensor. These values then make it possible to locate the detected defects. The length of the pipes and/or the distance between the sensors can also be known by other means, for example a connection plan.

The pipeline element 1 can be manufactured by first fixing the electrical bundle and the guided wave sensor 5 on the peripheral surface of the elementary pipe 3, then applying at least one layer of protective covering to the guided wave sensor and the bundle. Finally, the control electronics for the sensor 5 are fixed to the hollow profile body and connected to one end of the bundle.

Before the sensor 5 is fixed, the peripheral surface of the elementary pipe 3 can be covered with a protective covering except for at least one annular area, the electrical cable being covered with the protective covering. The sensor of the guided wave type is then fixed on the peripheral surface of said body, in said annular area.

Figure 2:
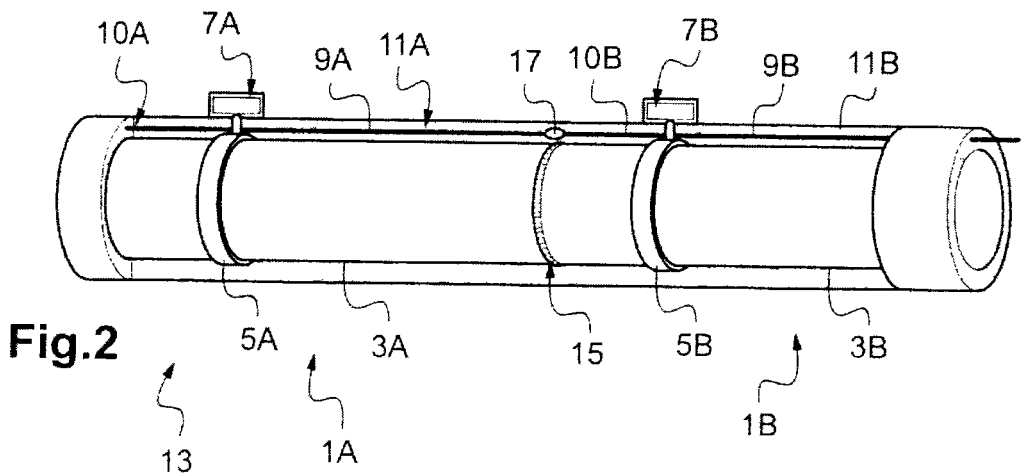
FIG. 2 shows a pipeline produced from elements of FIG. 1, seen in perspective and partially cutaway.

Reference is made to FIG. 2.

A section, or segment, of pipeline 13 was produced by connecting together the adjacent ends of a first pipeline element 1A, of the type of the pipeline element 1 of FIG. 1, and of a second pipeline element 1B, analogously. Here, the connection uses a weld seam 15 which produces a sealed join of the ends of the elementary pipes 3A and 3B facing each other.

An electrical junction 17 ensures a mutual connection of the first electrical bundle 9A of the first pipeline element 1A and the second electrical bundle 10B of the second pipeline element 1B. The electrical junction 17 can take the form of a flat connector or also of a welded joint between the respective ends of the electrical bundles.

In the section of pipeline 13, guided wave sensors 5A and 5B equipping the pipeline elements 1A and 1B are controlled by respective on-board electronics 7A and 7B, which are connected together via the second bundle 10B and the first bundle 9A so as to exchange data and electric power with each other.

Figure 3:
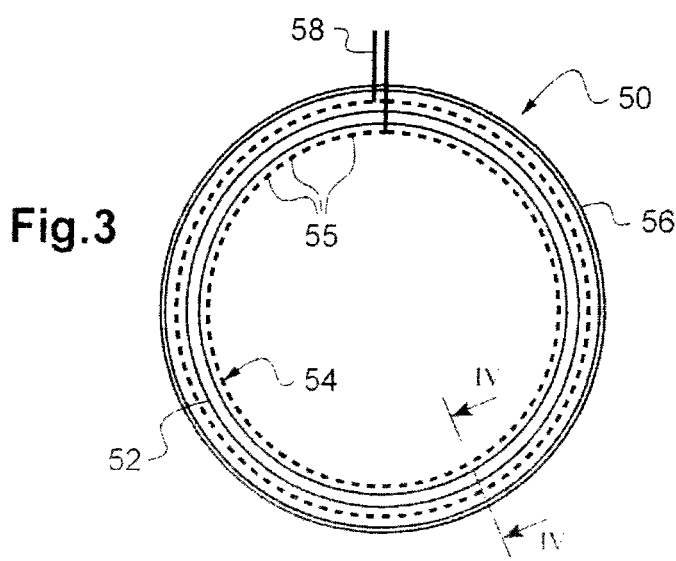
FIG. 3 shows a guided wave sensor for the pipeline element of FIG. 1, seen in cross section.
Figure 4:
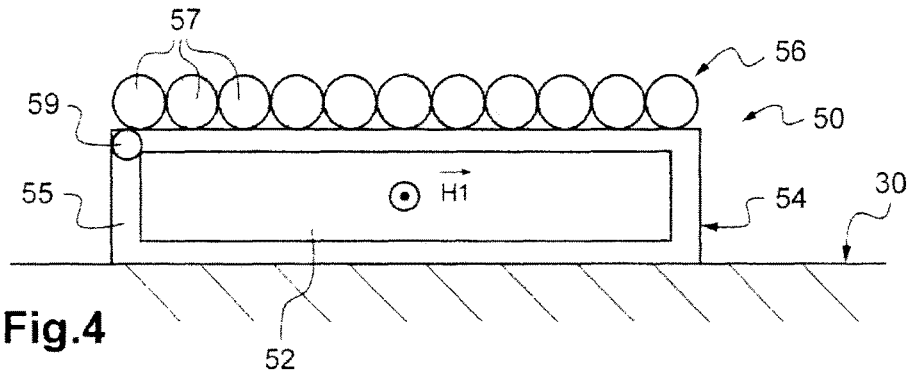
FIG. 4 shows the guided wave sensor of FIG. 3, seen in section along a line IV-IV.

Reference is made to FIGS. 3 and 4.

A magnetostrictive sensor 50 can be used as a guided wave sensor 5 for a pipeline element. The magnetostrictive sensor 50 comprises a section of a strip of magnetostrictive material 52, here having a substantially rectangular transverse section. The magnetostrictive strip 52 can in particular be produced from iron for example alloyed with nickel, for example alloyed with cobalt. For example, the magnetostrictive strip 52 is obtained from the material known as Hiperco50HS from the company Cartech or also from the material known as AFK502R from the company Arcelormittal, heat-treated. It can have the following composition (by mass):
Iron Fe: 48.8%,
Cobalt Co: 49%,
Vanadium V: 2%,
Niobium Nb: 0.2%

And the following properties (after heat treatment):
Deformation relating to saturation by magnetostriction: 60.10-6 inches
Curie temperature: 938° C.
Young's modulus: 73 ksi
Other magnetostrictive materials can be used, such as a Nickel alloy or an alloy of the type known as Terfenol-D.

The sensor 50 comprises a first coil 54 each winding 55 of which transversally surrounds the section of magnetostrictive strip 52. The section of magnetostrictive strip 52 is arranged inside the first coil 54, in such a way that the direction of winding of the first coil 54 substantially coincides with the longitudinal direction of the section of magnetostrictive strip 52.

The first coil 54 can be produced by winding an insulated conductive wire 59 (FIG. 4) around the magnetostrictive strip 52 so as to form the turns 55. The wire 59 can be fixed to the magnetostrictive strip 52, by means of glue or adhesive tape. As a variant, the magnetostrictive strip can be covered with an insulator and the wire 59, free of insulating sheath, wound directly on the strip covered in this way. In this case, the turns 55 are not contiguous. In this case, the assembly is covered with a layer of insulating material. The diameter of the wire 59 is such that this wire 59 can withstand current intensities of the order of several amps for several seconds without deteriorating. In yet another variant, the coil 54 can be produced in a flexible circuit of the PCB (for "printed circuit board") type.

By supplying the first coil 54 with a continuous electric current, a magnetic field H1 is generated within the magnetostrictive strip 52, directed in a longitudinal direction of the strip 52. The magnetic field H1 can be used to magnetize the section of magnetostrictive strip 52.

The diameter of the wire 59 is small enough to allow it to be wound in a large number of turns along the magnetostrictive strip 52. The magnetic field capable of being generated by the first coil 54 is then optimal. By way of example, the wire 59, here, has a diameter close to 0.32 millimeters.

The strip 52 is located where a magnetic field generated by the first coil 54 will be strongest, with constant current. Here, the windings 55 are in contact with the external surface of the section of magnetostrictive strip 52. They can be held fixedly in this relative position by means of glue or adhesive tape, for example.

The section of magnetostrictive strip 52, surrounded by the first coil 54, has a flexibility which allows it to be wrapped around a pipe transversally thereto. Here, the wrapping is done in one go. Each turn 55 of the first coil 54 is partially in contact with the external surface 30 of the pipe via a layer of fixing medium. The parts of the first coil 54 in contact with the surface 30 can be glued there.

The first coil 54 advantageously has, overall, an electrical resistance comprised between 5 and 50 ohms depending on the diameter of the tubular element on which it is installed.

The magnetostrictive sensor 50 also comprises a second coil 56, which is arranged facing the section of magnetostrictive strip 52. Here, the turns 57 of the second coil 56 are contiguous and arranged in an alignment direction which corresponds to a transverse direction of the strip 52.

The second coil 56 can be applied externally, radially onto the section of magnetostrictive strip 52 combined with the first coil 54. Each turn 57 is then substantially concentric to a transverse section of the pipe.

In an embodiment variant, the magnetostrictive sensor 50 comprises two second coils 56 arranged side-by-side. This makes it possible to direct the generated guided waves from one side of the sensor 50 to the other.

Again as a variant, the sensor 50 can comprise two elementary sensors, each constituted by a magnetostrictive strip 52, a first coil 54 wound around the latter and a respective second coil 56.

The first coil 54 can be supplied with power by a source capable of delivering a direct current of 2 amps at 70 to 80 volts in order to magnetize the magnetostrictive strip 52. This current originates from the on-board electronics 7.

The first coil 54 can also be supplied with current so as to demagnetize the magnetostrictive strip 52, in particular before each magnetization operation, such that the same magnetization state is obtained before each excitation of the magnetostrictive strip.

The second coil 56 can be supplied with power by a source capable of delivering a direct current of 30 amps at 300 volts in order to excite the magnetostrictive strip 52 with frequencies comprised between 32 and 250 kilohertz.

Figure 5:
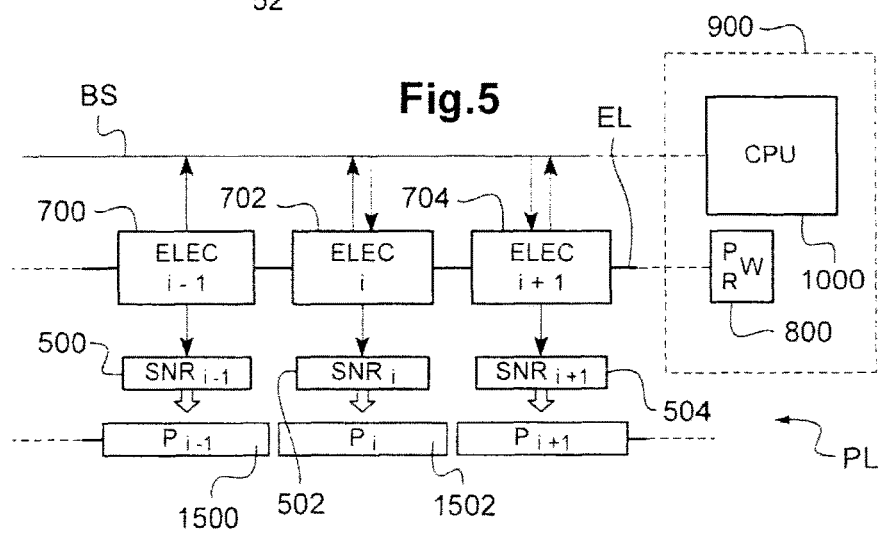
FIG. 5 shows a functional diagram of a network of sensors.

Reference is made to FIG. 5.

It shows a generic part of what can be called an intelligent pipeline network.

An elementary pipe Pi−1 is connected to a pipe Pi by means of a weld seam 1500. The pipe Pi is connected, at its end opposite the pipe Pi−1, to a pipe Pi+1 by means of another weld seam 1502. These elementary pipes form part of a pipeline of pipes PL.

The pipe Pi−1 is equipped with a generic sensor SNRi−1 500, and generic on-board electronics ELECi−1 700 which control this sensor, in order to form, together, a generic pipeline element.

Analogously, the pipe Pi is equipped with a sensor SNRi 502 controlled by electronics ELECi 702, and the pipe Pi+1 is equipped with a sensor SNRi+1 504 controlled by electronics ELECi+1 704.

The elementary pipes Pi−1, Pi, Pi+1 of the pipeline PL are each of the type of the pipeline element 1 described in relation to FIG. 1, at least when these elementary pipes are intended to be submerged. In particular, the sensors SNRi−1, SNRi+1 and SNRi are covered with a covering.

The on-board electronics ELECi are connected on the one hand to electronics ELECi−1 equipping the pipe Pi−1 and on the other hand to the electronics ELECi+1 equipping the pipe Pi+1 via:

- a bus BS for transmitting data useful for monitoring the pipeline PL to a processing computer CPU 1000, for example housed in a control room 900 on the surface or on a platform, and
- an electrical feed line EL connected to a current source PWR 800, for example housed in the control room 900.

From sensors SNRi and respective control electronics ELECi, connected together by a common data bus BS and a common electrical feed line EL, it is possible to create a network of sensors distributed over the length of the pipeline. The section of the electrical feed line EL and that of the data bus BS corresponding to the submerged elementary pipes are covered with a covering which also covers the sensors equipping these pipes and the corresponding bare pipes.

This network of sensors makes it possible to check the structure of the pipeline PL and of each of its elements on the basis of a chain of guided wave sensors associated with electronic boxes electrically connected together.

The bus BS can comprise an electrical bundle with four strands, optionally twisted, for the serial transmission of the information between the processing computer 1000 and each of the control electronics ELECi.

The electrical feed line EL can comprise an electrical bundle comprising two strands connected to a source of direct current of 24 volts at 2.5 amps for supplying power to the control electronics ELECi.

According to the tests performed by the Applicant, such a network can reach 400 meters in length. It is possible to produce networks extending over even longer distances. In order to communicate over such distances, the communication speed can be reduced.

Still according to the Applicant's tests, it is possible to equip a pipeline 2 kilometers in length with only a 60-watt generator, i.e. to supply 200 control electronics with power, while still having three of these electronics active.

Figure 6:
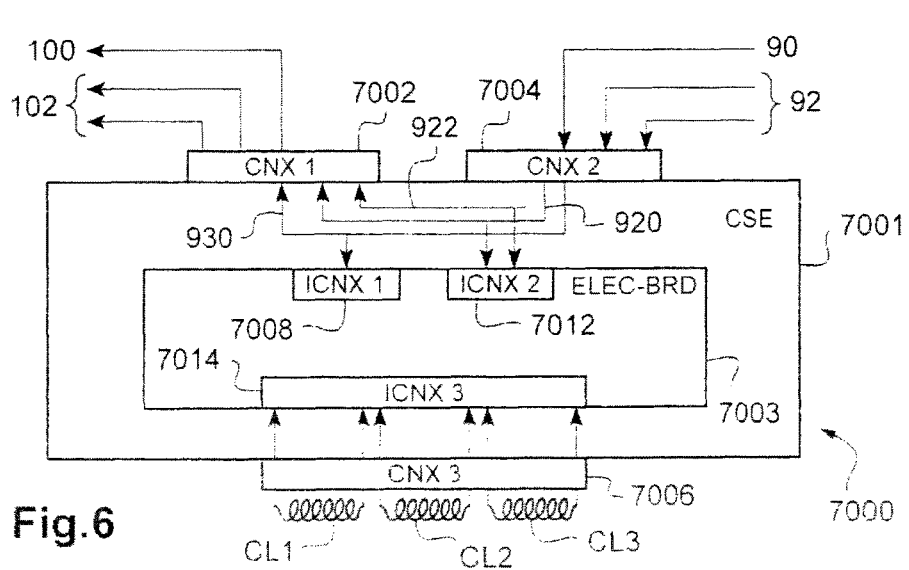
FIG. 6 shows an architecture diagram of an electronic box for the pipeline element of FIG. 1.

Reference is made to FIG. 6.

It shows an embodiment example of control electronics 7000 which can be used as on-board electronics in a pipeline element.

The electronics 7000 comprise a sealed box CSE 7001, here of the IP68 type, in order to prevent liquid from entering the box 7001, to which a first connector CNX1 7002, a second connector CNX2 7004 and a third connector CNX3 7006 are fixed, each of the IP 68 ATEX type to also prevent a spark from being created or explosive gas from coming into contact with a spark in the box.

Each of the first connector CNX1 7002 and the second connector CNX2 7004 comprises a respective data interface 90, 100, for example of the RS 485 type, and a respective power supply interface 92, 102 comprising two electrical lines jointly delivering a working voltage, for example 24 volts DC. The working voltage allows quite a low consumption and a low risk of explosion, compared with an alternating current of 220 volts, for example.

The third connector CNX3 7006 comprises an electrical connection interface with each of a first coil CL1, a second coil CL2, and a third coil CL3. For example, the first coil CL1 corresponds to a magnetization coil of a magnetostrictive sensor and the second CL2 and the third CL3 coils correspond to excitation coils of this sensor.

The power supply interface 92 of the second connector CNX2 7004 is electrically connected to the power supply interface 102 of the first connector CNX1 7002 by two electrical lines 920 and 922. The data interface 90 of the second connector CNX2 7004 is connected, in data communication, to the data interface 100 of the first connector CNX 1 7002 by a data line 930.

The data line 930 is connected to a data interface of a first internal connector ICNX1 7008. The electrical lines 920 and 922 are connected to a power supply interface of a second internal connector ICNX2 7012. The first internal connector ICNX1 7008 and the second internal connector ICNX2 7012 are attached to an electronic board 7003 housed in the box 7001. The electronic board ELEC-BRD 7003 is moreover equipped with a third internal connector ICNX3 7014 electrically connected to the third external connector CNX3 7006.

Figure 7:
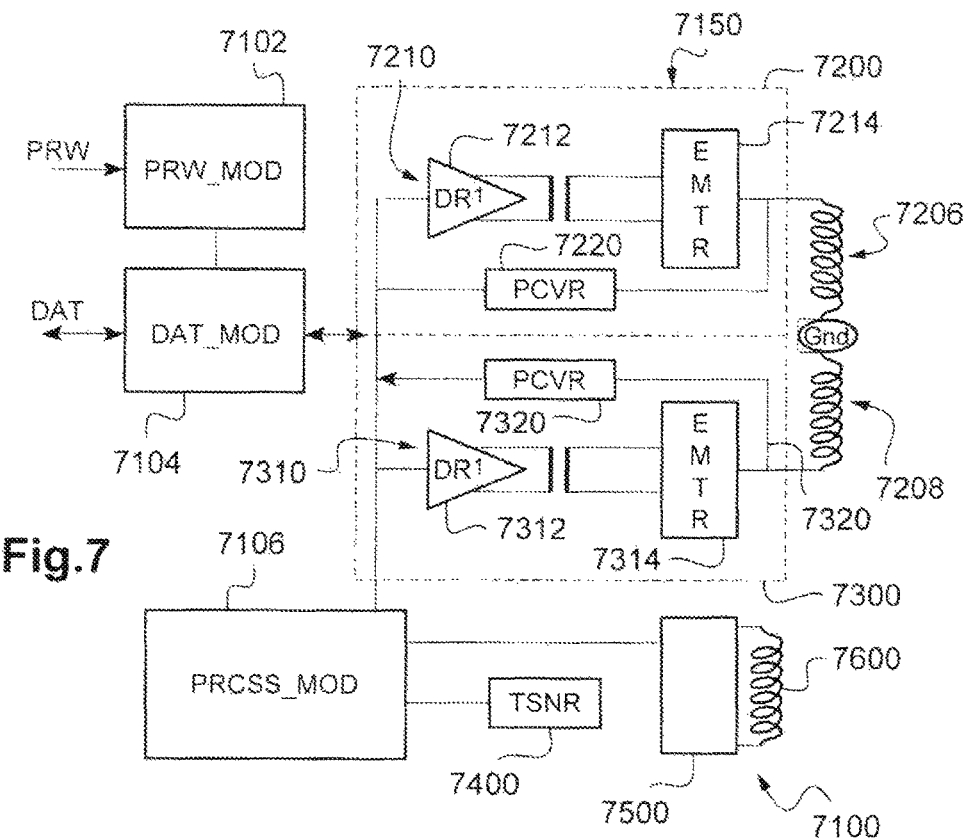
FIG. 7 shows a functional diagram of control electronics for the pipeline element of FIG. 1.

Reference is made to FIG. 7.

It shows a control circuit 7100 for a guided wave sensor, which can be implemented on the electronic board 7003 of FIG. 6.

The control circuit 7100 comprises a power supply module 7102, supplied with a direct current of 24 volts, such as is delivered for example to the second internal connector ICNX2 7012 of FIG. 6.

The total electrical consumption of the electronics can be reduced to 0.7 W in operation and to 0.3 W in a standby mode. A galvanic isolation is placed between the bus BS and the main electronics, for example of at least 4 kilovolts root mean square. A protection against electrostatic discharges of ±15 kilovolts is put in place for the inputs/outputs.

The power supply of the control circuit 7100 must be isolated from the 24 volt input. The output voltages delivered by the power supply module are for example 5, 24 and ±300 volts.

The control circuit 7100 moreover comprises a transmission module 7104 which receives data from the first connector ICNX1 7008 and transmits data to the latter.

The control circuit 7100 comprises a transmission/reception module 7150 capable of causing one or more transducers of a guided wave sensor to function. Here, the transmission/reception module 7150 comprises a first circuit 7200 intended for a first coil 7206 and a second circuit 7300 intended for a second coil 7208. The first circuit 7200 and the second circuit 7300 are analogous to each other, and are connected together at the output of a processing module 7106. The first coil 7206 and the second coil 7208 are for example excitation coils of a magnetostrictive sensor.

Each of the first circuit 7200 and the second circuit 7300 comprises a respective transmission path 7210, 7310 for exciting the first coil 7206 or the second coil 7208, and a respective reception path 7220, 7320 for the electrical signals received at the first coil 7206 or the second coil 7208. The transmission paths 7210 and 7310 can also be seen as excitation circuits of the first coil 7206 and of the second coil 7208, respectively.

The input of each transmission path 7210, 7310 is connected to an output of the processing module 7106. The output of each transmission path 7210, 7310 is connected to a terminal of the first coil 7206 or of the second coil 7208.

The output of each reception path 7220, 7320 is connected to an input of the processing module 7106. The input of each reception path 7220, 7320 is connected to the terminal in question of the first coil 7206 or of the second coil 7208.

Each transmission path 7210, 7310 comprises a respective driver 7212, 7312, the output of which is connected to a respective transmitter circuit 7214, 7314, the output of which is connected to the terminal in question of the first coil 7206 or of the second coil 7208.

The processing module 7106 is connected to a temperature sensor 7400 arranged inside the box 7001, as well as a magnetization module 7500 connected operationally to a respective coil 7600, for example a magnetization coil of a magnetostrictive sensor.

The magnetization module 7500 makes it possible to magnetize a magnetostrictive strip of a guided wave sensor. The duration of magnetization is programmed in the processing module 7106. Typically, this duration is less than 10 ms. Analogously, the intensity of the current delivered can be programmed in the processing module 7106, for example up to 3 amps. The time value of the delay between the start of the magnetization and the start of the excitation can also be regulated, for example between −1 and +9 milliseconds.

Figure 8:
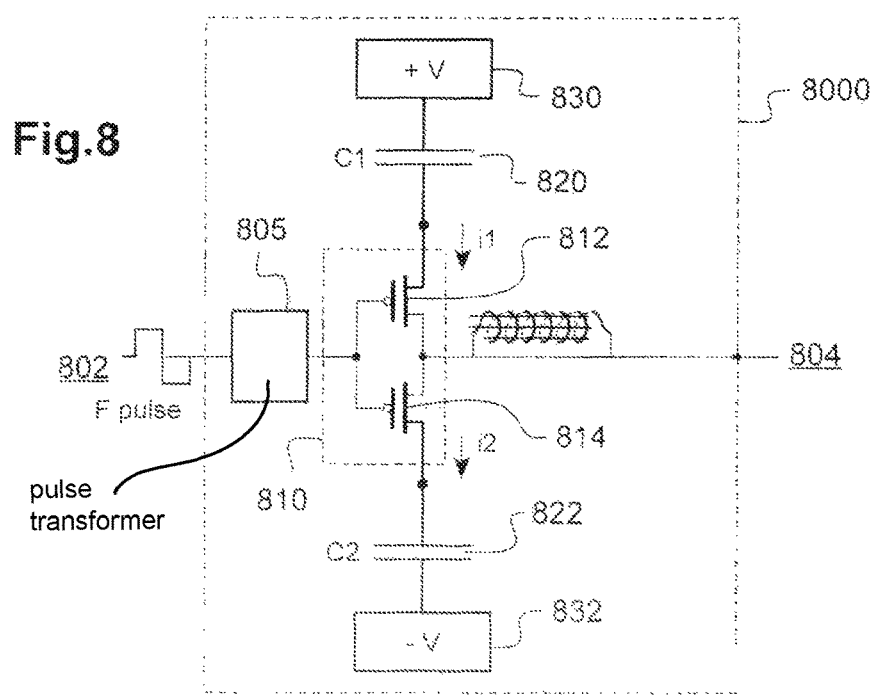
FIG. 8 shows a detailed functional diagram of a part of the electronics of FIG. 7.

Reference is made to FIG. 8.

It shows an electronic circuit 8000 which can be used as transmitter circuit, for example for the transmitter circuit 7214/7314 of FIG. 7.

The circuit 8000 comprises a pulse transformer 805, the input of which is connected to the input 802 of the circuit 8000, and the output of which is connected to the input of a half bridge 810 comprising a first transistor of the MOSFET type 812 and a second transistor of the MOSFET type 814. The drain of the first transistor 812 is connected to a first high-voltage capacitor 820, the drain of the second transistor 814 is connected to a second high-voltage capacitor 822. The source of the first transistor 812 and that of the second transistor 814 are connected to each other, and to the output 804 of the circuit 8000. The box 830 connected to the first capacitor 820 can deliver a voltage with a value +V, whereas the box 832 connected to the second capacitor 822 can deliver a voltage with a value −V. The output 804 of the circuit 8000 makes it possible to deliver a pulse voltage comprised between the values −V and +V. An adjustment, manual or programmed, can be integrated in order to adjust the voltage of the high-voltage electric power supply, typically between 50 and 300 volts.

A circuit, not shown, drives the transistors 812 and 814.

The circuit 8000 can function in three modes as a function of a received command, in particular from the processing module 7106, for example over a link of the RS485 type.

In a first operating mode, all of the elements are activated, and supplied with power, the high-voltage capacitors 820 and 822 are charged, and the circuit 8000 waits for a start message over the RS485 link. This is an initial state, which can be followed by a partial standby mode in which some parts of the circuit are no longer supplied with power and where only the elements for receiving communication data, for example, are activated.

In a second operating mode, called "transmission sequence", the pulse generator 805 transmits up to three pulses over the transistor bridge, at a frequency set by software, typically comprised between 10 and 256 kilohertz.

When the first transistor 812 is conductive, the first capacitor 820 is connected directly to the output 804, therefore to the corresponding excitation coil and discharges there with a high current, which can reach up to 30 amps.

Then, the power supply module recharges the first capacitor 820.

When the second transistor 814 is conductive, the second capacitor 814 is connected directly to the output 804, therefore to the corresponding excitation coil and discharges there with a high current, which can reach up to 30 amps.

Then, the power supply module recharges the second capacitor 822.

The discharge of the first capacitor 820 and of the second capacitor 822 is offset relative to each other by a half cycle.

The recharging of the first capacitor 820 and of the second capacitor 822 can be carried out in parallel to each other.

In the third operating mode, all of the components are powered off except for those which participate in the detection of the messages which are sent over the RS485 link.

Figure 9:
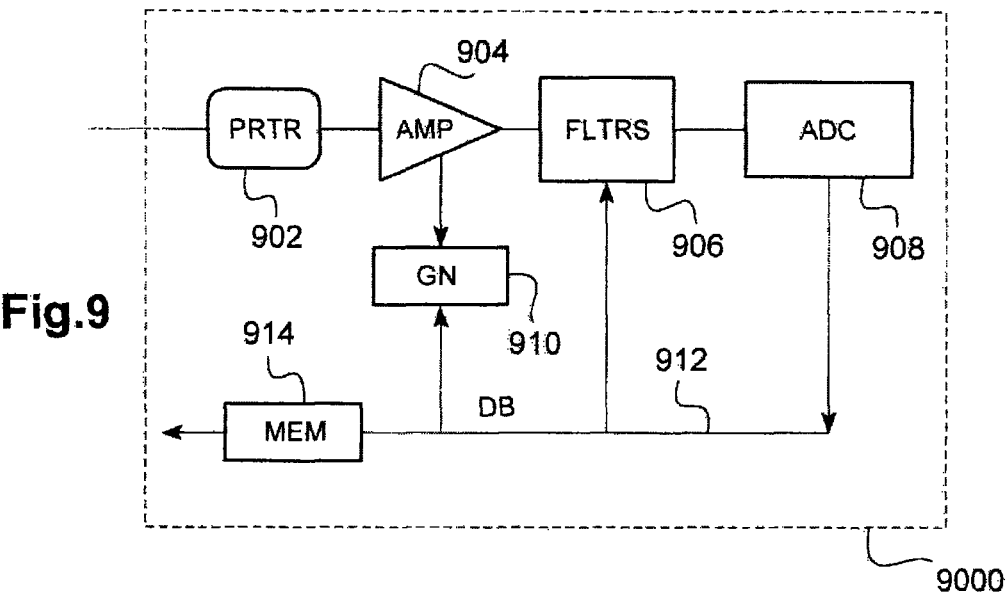
FIG. 9 shows a detailed functional diagram of another part of the electronics of FIG. 7.

Reference is made to FIG. 9.

It shows a circuit 9000 as an embodiment example of a reception circuit for an excitation coil, for example the reception path 7220 or 7320 of FIG. 7.

The circuit 9000 comprises a surge protection element 902, the input of which is connected to the excitation coil and the output of which is connected to the input of an amplifier 904. A first output of the amplifier 904 is connected to a programmable filter module 906, the output of which is connected to an analog-to-digital converter 908 of the 12 bits, 2.5 megahertz type.

The other output of the amplifier 904 is connected to a programmable gain module 910.

The output of the analog-to-digital converter 908 is connected to a data bus 912, itself connected to an input of the programmable filter module 906 and of the programmable gain module 910. The module supplies power, moreover, to a memory 914, for example a part of the memory of a microcontroller, which forms part for example of the processing module 7106. The gain is programmable digitally, for example up to 85 decibels.

Each of the filters of the filter module 906 is a second-order filter and has a passband comprised between 10 and 205 kilohertz. These filters are also programmable digitally.

Typically, the memory 914 comprises a minimum of 128 kilowords.

Figure 11:
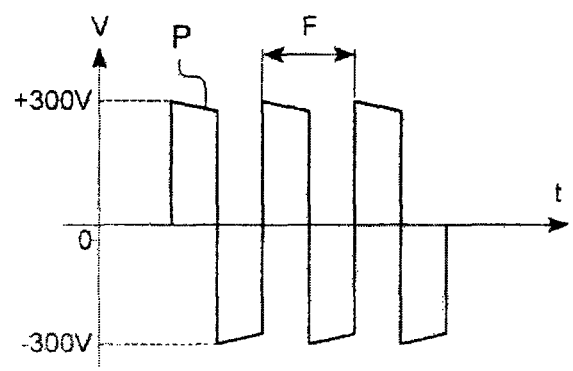
FIG. 11 shows a functional diagram of a data processing module for the electronics of FIG. 7.

Reference is made to FIG. 11.

The processing module 7106 comprises a transmission sub-module 7301 which formats the data with a view to transmitting them and implements the communication protocol, a receiving gain regulating sub-module 7302, an energy management module 7303, a magnetization sub-module 7304 which controls a magnetization circuit, for example the circuit 7500 of FIG. 7, a control sub-module of programmable filters 7305. The processing module 7106 moreover comprises a decoding sub-module 7306 capable of identifying an address value specific to it in a received message, a temperature acquisition sub-module 7307 which interacts with a temperature sensor, for example the sensor 7400 of FIG. 7, a transmission sub-module 7308 which controls transmission paths, for example those of the first circuit 7200 and of the second circuit 7300 of FIG. 7, and an acquisition sub-module 7309 which receives and processes the signals received from the reception paths, for example the paths 7220 and 7320 of the first circuit 7200 and of the second circuit 7300 of FIG. 7.

Figure 10:
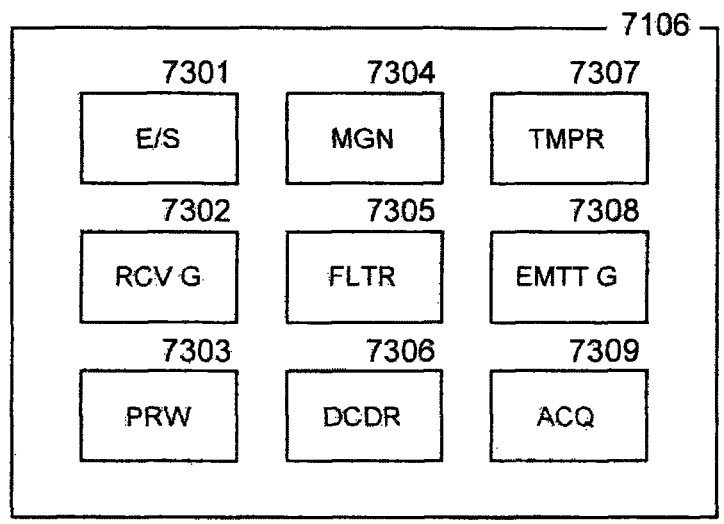
FIG. 10 shows a supply voltage timing diagram which can be implemented in the electronics of FIG. 7.

Reference is made to FIG. 10 in conjunction with FIG. 11.

The transmission sub-module 7308 is arranged to control a series of alternating electrical pulses P with an amplitude comprised between −300 and +300 volts and a period F. The period F is parameterizable. The form of the series of pulses is also parameterizable, in particular as regards the regulation of the number of pulses and the time separating two consecutive pulses.

The energy management module 7306 is arranged to automatically put the system on automatic standby.

The processing computer CPU 1000 can be arranged to execute a calibration function.

In a first step, the processing computer 1000 actuates the transmission of a series of pulses to a sensor of the pipeline to be calibrated, which is denoted sensor A. The shape of these pulses for example conforms to FIG. 10. Each pulse is transmitted with a first gain value, which is denoted value GEA0.

In a second step, a sensor adjacent to the sensor A, which is denoted sensor B, receives a signal with an initial gain value, or value GRB0. The value GRB0 is sent to the processing computer 1000, which increases, or reduces, the value of the transmission gain of the sensor A until the receiving gain of the sensor B is close to a predefined gain value, or value GRB1.

In a third step, the processing computer 1000 controls the transmission of a series of pulses by the sensor B, with a gain of value GEB0, which can be close to the value GEA0 of the transmission gain. A value of the receiving gain at the sensor A, which is denoted GRA0, is measured. In order to reach the gain value GRB0 at the sensor A, the transmission gain of the sensor B is adjusted. The adjustment of each receiving gain ensures that a signal will always be received with the same intensity and therefore uniformity of the measurements carried out.

As a variant or in addition, the processing unit 1000 can be arranged to execute a calibration function.

The processing unit 1000 can moreover be configured to monitor the temporal evolution of the time taken for the echo to travel from the sensor A to the sensor B. The variation in the travel time can be correlated to a variation in temperature, or to the speed of propagation of the waves since, from the point of view of the guided waves, the distance DO is fixed throughout the life of the pipeline. This makes it possible moreover to compare echoes with each other, even if the temperature varies between the measurements.

The variations in temperature at the pipeline affect the speed of propagation of the different guided wave packets. They can result in an expansion or contraction of the signal. Such a phenomenon can cause a time difference between a measurement signal and a reference signal, when these are recorded at different temperatures. As a result, subtracting the reference signal from the measurement signal can lead to a significant difference.

Because the distance between the sensors is fixed, a coefficient of expansion/compression can be calculated between a signal taken as reference and a subsequent signal, such that the difference between them makes it possible to show the appearance, or not, of an additional peak revealing the presence of a defect. The method known as "Optimal Stretch" can thus be applied.

The methods for stretching (or compressing) the signal in order to compensate for the change in temperature can be applied to the reference signal or the measurement signal, in order to obtain a better correspondence between the two signals on which the subtraction is to be performed.

The invention is not limited to the embodiments described above, by way of example only, but encompasses all of the variants that can be imagined by a person skilled in the art, and in particular:

- The guided wave sensor 5 can be free of electrical connection and can then comprise only a passive part arranged under the covering 11. In this case, an active part is fixed on the elementary pipe 3, for example by clamping, at the time of the installation of the electronics 7 on the elementary pipe 3. This operation can be performed for example just before putting it in the water for offshore applications.
- The electronics 7 can be arranged, at least partially, outside the covering 11.
- The body 2 can be produced by connecting several bare pipes to each other.
- In some cases, in particular if the magnetostrictive characteristics of the elementary pipe 3 are sufficient, the guided wave sensor 5 can be free of magnetostrictive strip and/or of magnetization coil. In this case, the guided wave sensor 5 can comprise only an excitation coil.
- In some embodiments, the guided wave sensor 5 can be produced in the form of an electroplating or a localized treatment on the external surface of the elementary pipe 3 in order to locally increase the magnetostrictive properties of the steel.
- The welded joint connecting two pipeline elements together can function as a guided wave sensor 5, when this welded joint is capable of generating guided waves.
- The guided wave sensor 5 can be combined with additional sensors such as, for example, a strain gauge, a temperature gauge. In particular, the guided wave sensor 5 can be combined with optical fibre sensors.
- A pipeline element 1 can be produced by connecting several pipeline elements to each other. When a pipeline element 1 comprises several sensors 5, not all of the sensors 5 are necessarily covered with the protective covering. In particular, the sensors 5 closest to the ends of the element can be left bare and can be covered after said end is welded onto the pipeline, so that the pipeline can be put in place.
- The power supply can be provided by other techniques, such as for example the use of a temperature gradient between the transported fluid and the surrounding medium, applying the Peltier effect.

At least one of the cables can be replaced with one or more optical fibres and can participate in the monitoring as an additional sensor.

The expression "homologous pipeline elements" denotes elements which can be mechanically combined, and fitted with sensors and/or electronics allowing them to work together, in particular to communicate. These are not necessarily absolutely identical sensors and/or electronics.

When it is fitted with an active coil and a magnetostrictive strip, the sensor 5 is capable of generating guided waves on both sides of this coil, in a symmetrical manner. The frequency of the current passed through this coil corresponds to the main frequency of the transmitted wave.

When it is fitted with two active coils and two magnetostrictive strips, the sensor 5 is capable of being implemented according to the technique known as "direction control".

In this technique, the active coils are separated from each other by lambda/4, where lambda represents the length of the guided wave that is provided to be used for the check. This makes it possible, by design, to cancel the signal sent from one side of the sensor 5 and to double the signal sent from the other side. This technique is advantageous in that it conventionally makes it possible to locate defects. Nevertheless, it requires an excitation frequency which may not be optimal for detecting certain defects.

Here, the sensor 5 can use only a single coil, excited at all of the frequencies comprised within the range mentioned above. Advantageously, the excitation frequency is made to vary until the echo is maximized, given that the length of the defect and the thickness of the covering 11 influence the amplitude of the peak generated by the defect as a function of the frequency. The location of the defect in question is obtained by cross-checking the inspection data of several consecutive sensors.

According to an embodiment of the invention, illustrated for example in FIG. 1, an element to be connected to a pipeline comprises a pipe equipped with a sensor 5 situated close to one of the ends of this pipe. For example, the sensor is arranged 2.2 meters from the end of the pipe. According to an embodiment variant, the element to be connected comprises several pipes connected together and each comprising a sensor 5. Each sensor is arranged 2.2 meters from one end of its respective pipe, with the exception of the sensor of one of the pipes situated at the end of the element, which sensor is arranged even closer to the end of this pipe. In this case, the sensor in question can be covered at the same time as the welded joint which connects the element to the pipeline.

The hollow profile body 3 of the pipeline element 1 can comprise at least two hollow profile elements connected together.

At least a part of the protective covering 11 of the pipeline element 1 can be arranged under the guided wave sensor 5 and/or under the electrical cable 9.

The protective covering 11 can be of the multi-layer type and at least one of said layers is intercalated between the guided wave sensor 5 and/or the electrical cable 9 and the external surface of the hollow profile body 3. Said layer can have adhesive properties such that it ensures that the guided wave sensor 5 and/or the electrical cable 9 are fixed to the external surface of the hollow profile body 3, at least partially.

The electrical cable can be spirally wound around the hollow profile body, from the control electronics 7 up to one end of the body 3 of the pipeline element 1.

The control electronics 7 can comprise a first circuit capable of supplying power to the excitation coil, and a second circuit capable of supplying power to the magnetization coil.

In order to fix at least one electrical cable and one sensor of the guided wave type on a peripheral surface of a hollow profile body, a hollow profile body 3 with a peripheral surface that is covered with a protective covering except for at least one annular area can be provided, the electrical cable being covered by the protective covering, and a sensor of the guided wave type 5 can be fixed on the peripheral surface of said body 3, in said annular area.

The invention claimed is:

1. An element configured to be mounted at one end of a pipeline configured for circulation of fluid, to extend the pipeline, the element comprising:
a hollow profile body including an external peripheral surface;
a protective covering at least partially covering the peripheral surface;
a guided wave sensor;
control electronics for the guided wave sensor; and
at least one electrical cable,
wherein both the control electronics and the at least one electrical cable are configured to connect the control electronics to homologous electronics of the pipeline,
wherein the at least one electrical cable and the guided wave sensor are fixed to the peripheral surface of the hollow profile body, under at least a part of the protective covering, and
wherein at least a part of the protective covering is arranged under the guided wave sensor and/or under the at least one electrical cable.

2. An element according to claim 1, wherein the protective covering covers all of the peripheral surface of the hollow profile body except for an area neighbouring each of longitudinal ends of the hollow profile body.

3. An element according to claim 1, wherein the guided wave sensor is close to one end of the hollow profile body.

4. An element according to claim 1, wherein the hollow profile body comprises at least two hollow profile elements connected together.

5. An element according to claim 1, wherein the protective covering includes a plurality of layers and at least one of the layers is inserted between the guided wave sensor and/or the at least one electrical cable and the external peripheral surface of the hollow profile body.

6. An element according to claim 5, wherein the at least one layer has adhesive properties to fix the guided wave sensor and/or the electrical cable to the external peripheral surface of the hollow profile body, at least partially.

7. An element according to claim 1, wherein the at least one electrical cable is spirally wound around the hollow profile body, from the control electronics to one end of the hollow profile body.

8. An element according to claim 1, wherein the control electronics comprise an excitation circuit for the guided wave sensor.

9. An element according to claim 1, wherein the guided wave sensor comprises an assembly formed of a magnetostrictive strip, an excitation coil, and a magnetization coil for the magnetostrictive strip.

10. An element according to claim 9, wherein the control electronics comprise a first circuit configured to supply power to the excitation coil, and a second circuit configured to supply power to the magnetization coil.

11. A pipeline configured for circulation of fluid comprising:
- a plurality of elements joined together end to end and each of the plurality of elements comprising: a hollow profile body including a peripheral surface and a protective covering at least partially covering the peripheral surface,
- wherein at least some of the elements comprise a guided wave sensor fixed to the hollow profile body, control electronics for the guided wave sensor, and electrical cables,
- wherein both the control electronics and the electrical cables are configured to connect the control electronics to homologous electronics of the pipeline,
- wherein the electrical cables and the guided wave sensors are fixed on the peripheral surface of a respective body, under at least a part of the protective covering, and
- wherein at least a part of the protective covering is arranged under the guided wave sensor and/or under the at least one electrical cable.

12. A pipeline according to claim 11, wherein at least some of the elements comprising the guided wave sensor are submerged.

* * * * *